United States Patent
Kawata et al.

(10) Patent No.: US 10,154,821 B2
(45) Date of Patent: Dec. 18, 2018

(54) RADIATION MEASURING APPARATUS, COMPUTER PROGRAM PRODUCT, AND RADIATION COMPUTED TOMOGRAPHY APPARATUS

(71) Applicant: Kabushiki Kaisha Toshiba, Minato-ku (JP)

(72) Inventors: Go Kawata, Kawasaki (JP); Yasuharu Hosono, Kawasaki (JP); Rei Hasegawa, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 178 days.

(21) Appl. No.: 15/259,739

(22) Filed: Sep. 8, 2016

(65) Prior Publication Data
US 2016/0374629 A1    Dec. 29, 2016

Related U.S. Application Data

(63) Continuation of application No. PCT/JP2015/057201, filed on Mar. 11, 2015.

(30) Foreign Application Priority Data

Mar. 24, 2014    (JP) .................................. 2014-060172

(51) Int. Cl.
*A61B 6/00*    (2006.01)
*A61B 6/03*    (2006.01)
(Continued)

(52) U.S. Cl.
CPC ................ *A61B 6/032* (2013.01); *A61B 6/06* (2013.01); *A61B 6/4035* (2013.01);
(Continued)

(58) Field of Classification Search
CPC ......... A61B 6/032; A61B 6/06; A61B 6/4035; A61B 6/4241; A61B 6/4435; A61B 6/465;
(Continued)

(56) References Cited

U.S. PATENT DOCUMENTS

2007/0228267 A1* 10/2007 Yokoi ................... G01T 1/1644
                                                              250/252.1
2009/0309031 A1   12/2009 Ohtani
(Continued)

FOREIGN PATENT DOCUMENTS

| JP | 2000-180390 | 6/2000 |
| JP | 3566398 B2  | 6/2004 |

(Continued)

OTHER PUBLICATIONS

Written Opinion dated May 26, 2015 in PCT/JP2015/057201 filed Mar. 11, 2015 (submitting English translation only, Japanese language previously filed).

(Continued)

*Primary Examiner* — Chih-Cheng Kao
(74) *Attorney, Agent, or Firm* — Oblon, McClelland, Maier & Neustadt, L.L.P.

(57) ABSTRACT

According to an embodiment, an apparatus includes a reference calculator, a peak calculator, a coefficient calculator, and a calibrator. The reference calculator is configured to calculate, as a first value, a most frequent electrical signal level from a first set of electrical signal levels output from the respective pixels of a detector for radiation. The peak calculator is configured to calculate, as a second value, a peak level of radiation energy of a characteristic X-ray, based on a relation between energy and intensity of radiation obtained from the first set. The coefficient calculator is configured to calculate a coefficient by dividing a difference (Continued)

between the first and second values by the peak level. The calibrator is configured to multiply an electrical signal level of each pixel by the coefficient and add the first value to the multiplication to calibrate a relation between detection output and incident radiation of the detector.

7 Claims, 12 Drawing Sheets

(51) Int. Cl.
*A61B 6/06* (2006.01)
*G01T 1/36* (2006.01)
*G01T 7/00* (2006.01)

(52) U.S. Cl.
CPC .......... *A61B 6/4241* (2013.01); *A61B 6/4435* (2013.01); *A61B 6/465* (2013.01); *A61B 6/467* (2013.01); *A61B 6/5205* (2013.01); *A61B 6/54* (2013.01); *A61B 6/585* (2013.01); *G01T 1/36* (2013.01); *G01T 7/005* (2013.01)

(58) Field of Classification Search
CPC .......... A61B 6/467; A61B 6/5205; A61B 6/54; A61B 6/585; G01T 1/36; G01T 7/005
See application file for complete search history.

(56) References Cited

U.S. PATENT DOCUMENTS

| 2011/0012014 A1* | 1/2011 | Livne | A61B 6/032 250/252.1 |
| 2014/0105370 A1* | 4/2014 | Yamakawa | A61B 6/025 378/207 |
| 2014/0284478 A1 | 9/2014 | Sako et al. | |
| 2017/0258412 A1* | 9/2017 | Daerr | A61B 6/032 |

FOREIGN PATENT DOCUMENTS

| JP | 2004-325183 A | 11/2004 |
| JP | 2007-271406 A | 10/2007 |
| JP | 2009-243998 | 10/2009 |
| JP | 2014-209098 | 11/2014 |
| WO | WO 2008/018264 A1 | 2/2008 |

OTHER PUBLICATIONS

International Search Report dated May 26, 2015 in PCT/JP2015/057201, filed on Mar. 11, 2015 (with English Translation).
Written Opinion dated May 26, 2015 in PCT/JP2015/057201, filed on Mar. 11, 2015.

* cited by examiner

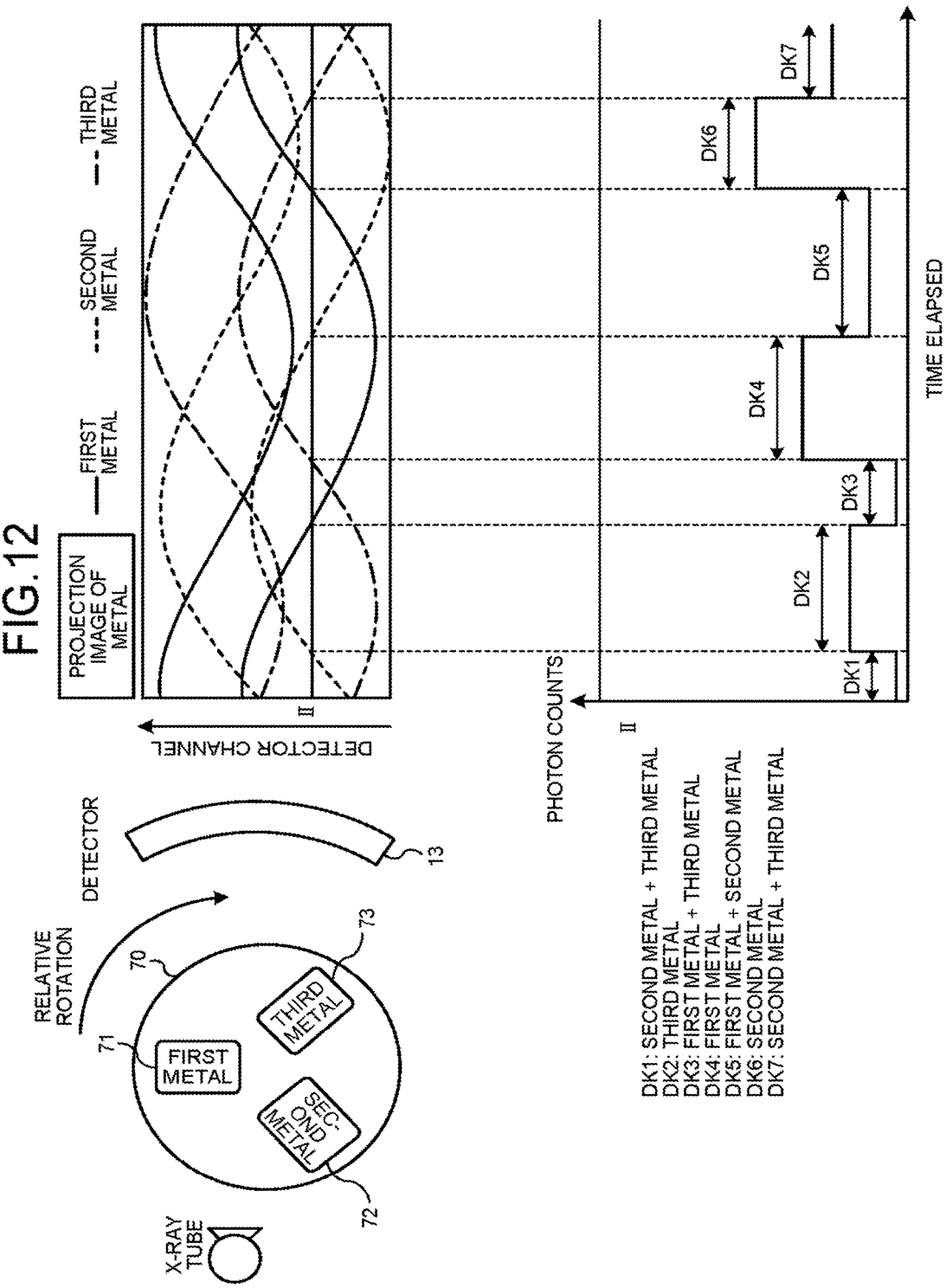

RADIATION MEASURING APPARATUS, COMPUTER PROGRAM PRODUCT, AND RADIATION COMPUTED TOMOGRAPHY APPARATUS

CROSS-REFERENCE TO RELATED APPLICATIONS

This application is a continuation of PCT international application Ser. No. PCT/JP2015/057201 filed on Mar. 11, 2015, which designates the United States, and which claims the benefit of priority from Japanese Patent Application No. 2014-060172, filed on Mar. 24, 2014; the entire contents of which are incorporated herein by reference.

FIELD

Embodiments described herein relate generally to a radiation measuring apparatus, computer program product, and a radiation computed tomography apparatus.

BACKGROUND

At present, photon counting computed tomography (CT) systems having photon counting detectors are known. A photon counting detector outputs a signal capable of individually counting X-ray photons having passed through a subject, unlike an integration detector. A photon counting CT system is thus capable of reconstructing an X-ray CT image having a high signal to noise ratio (SNR).

Signals output from a photon counting detector can be used for measurement (discrimination) of energy of X-ray photons. Thus, a photon counting CT system is capable of dividing projection data, which have been collected by emitting X-rays at one tube voltage, into a plurality of energy components to form an image.

Note that it is essential for measuring X-ray photons having passed through a material and discriminating an object material to calibrate the relation between an output from a radiation detector (a detector output) and the X-ray photon energy incident on the radiation detector (incident energy). Specifically, in a case of what is called an indirect conversion radiation detector, variations in the characteristics (multiplication rate, operating temperatures, etc.) of SiPM elements and variations in scintillation light detection efficiency (variations in detector geometric structure) are caused. Calibration between the output of the detector and incident energy is therefore required. Note that an indirect conversion radiation detector is a radiation detector configured to convert incident X-ray photons into scintillation photons by a scintillator, multiply the scintillation photons by solid silicon photomultiplier elements (SiPM: Silicon Photomultipliers), and output the multiplication result.

In related art, a plurality of checking source (radioactive isotopes) whose energy levels are known are used to identify a peak position in a pulse height distribution for each calibration energy level (a mode in a pulse height distribution), so as to calibrate a detector output and incident energy in association with each other.

In the case of calibration using calibration sources, however, the time required for calibration is determined by the amount of radiation from the calibration sources and the number of available calibration sources. Thus, a radiation detector having an enormous number of pixels such as hundreds of thousands of pixels, for example, has such problems as the number of elements calibrated per unit time being small and the time required for product shipment and apparatus maintenance being long.

In addition, while the calibration work is usually carried out before shipment of radiation detectors (or CT systems), the balance of the output and the incident energy of a calibrated detector may be lost owing to deterioration with time. Since, however, a long time is required for calibration as described above, it is very difficult to stop a CT system for a long time during surgery hours of a hospital to perform calibration again. For a similar reason, it is also difficult to periodically test and calibrate a radiation detector (or a CT system) after being delivered to a hospital.

Furthermore, there are few types of calibration sources supporting energy regions used for calibration. Specifically, while a low energy region of about 50 keV to 120 keV, for example, is used for calibration, calibration sources such as cesium having a long half-life do not support this energy region, and it is therefore difficult to use them as calibration sources. In contrast, in a case of calibration sources where cobalt 57 supporting the aforementioned energy region is used, the half-life is about 271 days, which is very short. Thus, when cobalt 57 is to be used as calibration sources, the calibration sources that are as new as possible need to be always ready in view of the half-life. This is unrealistic in terms of storage area, cost, and the like.

BRIEF DESCRIPTION OF THE DRAWINGS

FIG. 12 is a sectional view illustrating another example of a phantom image by the photon counting CT system of the second embodiment and a projection image.

DETAILED DESCRIPTION

According to an embodiment, a radiation measuring apparatus includes a detector, a reference calculator, a peak calculator, a coefficient calculator, and a calibrator. The detector has a plurality of pixels each including a plurality of detecting elements each configured to output an electrical signal level associated with incident radiation energy. The reference calculator is configured to calculate, as a first value, a most frequent electrical signal level from a first set of electrical signal levels output from the respective pixels. The peak calculator is configured to calculate, as a second value, an electrical signal level corresponding to a peak level of radiation energy of a first characteristic X-ray, based on a relation between a radiation energy and a radiation intensity obtained from the first set. The coefficient calculator is configured to calculate a coefficient obtained by dividing a difference between the first value and the second value by the peak level of the radiation energy of the first characteristic X-ray. The calibrator is configured to multiply an electrical signal level output from each of the pixels by the coefficient and add the first value to a value obtained by the multiplication to calibrate a relation between a detection output of the detector and radiation incident on the detector.

Hereinafter, embodiments to which a radiation measuring apparatus and an input/output calibration program are applied will be described in detail with reference to the drawings. Hereinafter, a photon counting CT system to which a radiation measuring apparatus and an input/output calibration program are applied and which is provided with an "indirect conversion detector" configured to convert scintillator light corresponding to X-ray photons into charge will be described as an example in detail with reference to the drawings.

First Embodiment

A photon counting CT system counts photons from X-rays (X-ray photons) having passed through a subject by using a photon counting detector to reconstruct X-ray CT image data having a high SNR. Individual photons have different energies. The photon counting CT system measures energy levels of photons to obtain information on X-ray energy components. The photon counting CT system divides projection data, which have been collected by driving X-ray tubes at one tube voltage, into a plurality of energy components to form an image.

Figure 1:
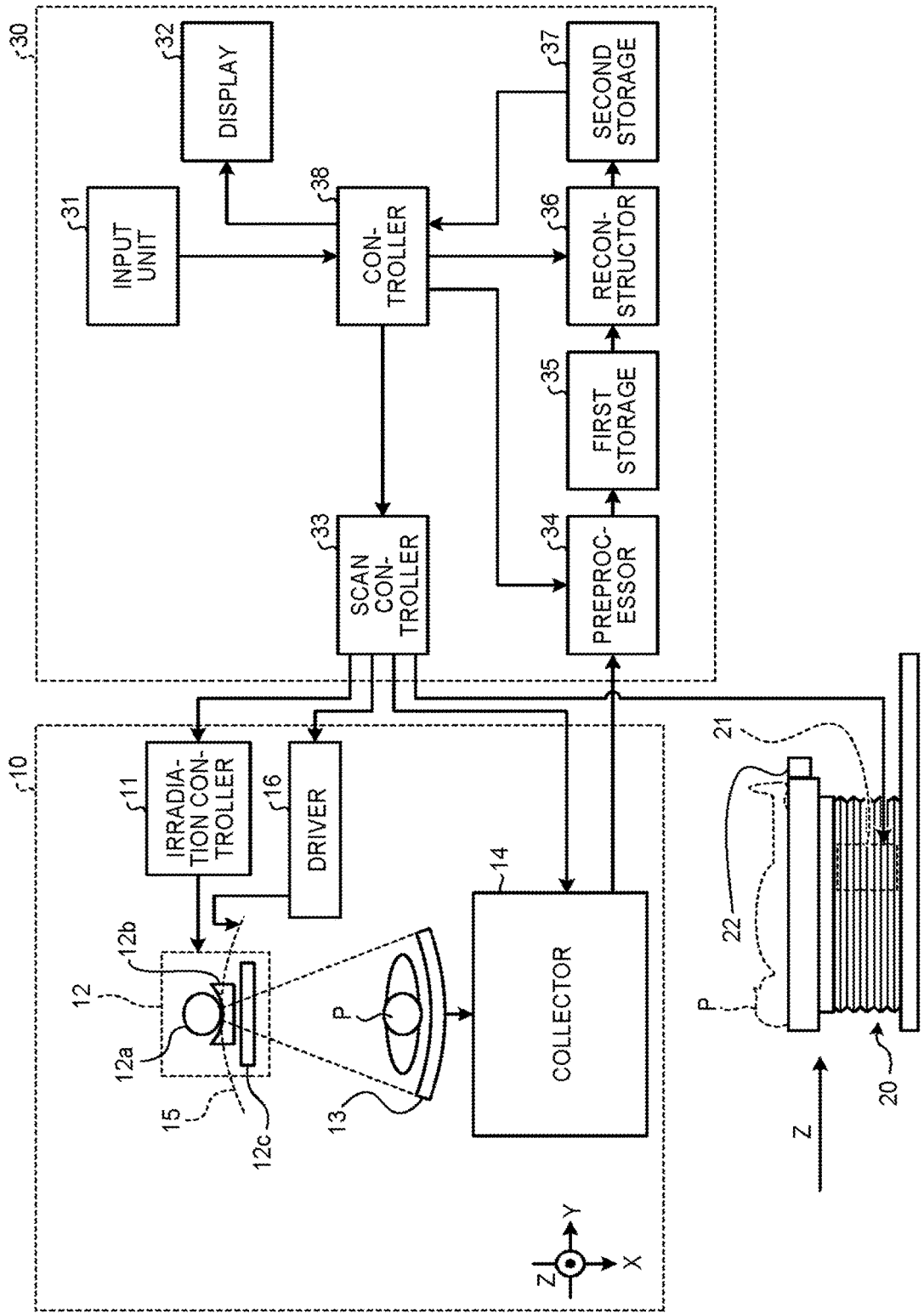
FIG. 1 is a diagram illustrating a configuration of a photon counting CT system of a first embodiment.

FIG. 1 illustrates a configuration of the photon counting CT system of the first embodiment. As illustrated in FIG. 1, the photon counting CT system includes a gantry 10, a bed 20, and a console 30.

The gantry 10 includes an irradiation controller 11, an X-ray generator 12, a detector 13, a collector (DAS: data acquisition system) 14, a rotatable frame 15, and a driver 16. The gantry 10 emits X-rays to a phantom P, and counts the number of X-rays having passed through the phantom P (or a subject). The detector 13 includes a plurality of pixels, each of which includes a plurality of detecting elements each configure to output an electrical signal level associated with incident radiation energy.

The rotatable frame 15 supports the X-ray generator 12 and the detector 13 so that the X-ray generator 12 and the detector 13 are opposed to each other with the phantom P therebetween. The rotatable frame 15 is an annular frame rotated at a high speed along a circular path around the phantom P by the driver 16, which will be described later.

The X-ray generator 12 includes an X-ray tube 12a, a wedge 12b, and a collimator 12c. The X-ray generator 12 is a device for emitting X-rays to the phantom P. The X-ray tube 12a is a vacuum tube for emitting X-rays to the phantom P by using high voltage supplied from the X-ray generator 12, which will be described later. The X-ray tube 12a emits X-ray beams to the phantom P while rotating with the rotation of the rotatable frame 15. The X-ray tube 12a generates X-ray beams spreading at a fan angle and a cone angle.

The wedge 12b is an X-ray filter for adjusting the amount of X-rays emitted from the X-ray tube 12a. Specifically, the wedge 12b is a filter that transmits and attenuates X-rays emitted from the X-ray tube 12a to the phantom P so that the distribution of the X-rays emitted from the X-ray tube 12a becomes a predetermined distribution.

For example, the wedge 12b is a filter made by processing aluminum to have a predetermined target angle and a predetermined thickness. Note that the wedge is also called a wedge filter or a bow-tie filter. The collimator 12c is a slit for narrowing the emission range of X-rays whose amount is adjusted by the wedge 12b under the control of the irradiation controller 11, which will be described later.

The irradiation controller 11 is a device serving as a high voltage generating unit to supply a high voltage to the X-ray tube 12a, and the X-ray tube 12a uses the high voltage supplied from the irradiation controller 11 to generate X-rays. The irradiation controller 11 adjusts a tube voltage and a tube current to be supplied to the X-ray tube 12a to adjust the amount of X-rays emitted to the phantom P. The irradiation controller 11 also adjusts the aperture of the collimator 12c to adjust the X-ray emission range (the fan angle and the cone angle).

The driver 16 rotates the rotatable frame 15 to cause the X-ray generator 12 and the detector 13 to rotate along a circular path around the phantom P. Each time an X-ray photon enters the detector 13, the detector 13 outputs a signal allowing measurement of the energy level of the X-ray photon. The X-ray photons are, for example, X-ray photons emitted from the X-ray tube 12a and passing through the phantom P. The detector 13 includes a plurality of detecting elements, each of which outputs a one-pulse electrical signal (analog signal) each time an X-ray photon enters the detecting element. The number of X-ray photons having entered each detecting element can be counted by counting the number of electrical signals (pulses). Furthermore, the energy level of an X-ray photon that caused a signal to be output can be measured through predetermined computation on the signal.

The detecting elements of the detector 13 are constituted by scintillators and photosensors such as photomultiplier elements (SiPM: Silicon Photomultipliers). The detector 13 is what is called an "indirect-conversion detector". The detector 13 first converts X-ray photons incident thereon into scintillator light by the scintillators, and then converts the scintillator light into electrical signals by the photosensors such as photomultiplier elements.

Figure 2:
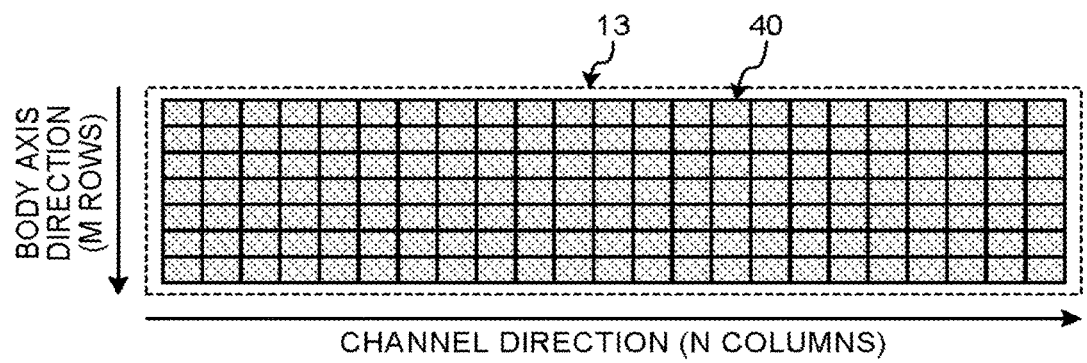
FIG. 2 is a plan view of a detector provided in the photon counting CT system of the first embodiment.

FIG. 2 illustrates an example of the detector 13. The detector 13 is an area detector in which the detecting elements 40 constituted by scintillators and photosensors such as photomultiplier elements are arranged in N columns in a channel direction (in a Y-axis direction in FIG. 1) and M rows in a body axis direction (in a Z-axis direction in FIG. 1). The detecting elements 40 each output a one-pulse electrical signal when a photon is incident on the detecting element 40. Individual pulses output by the detecting elements 40 are discriminated from one another, which enables counting of the number of X-ray photons incident on the detecting elements 40. In addition, measurement of the energy levels of the counted X-ray photons can be performed by computation based on the intensities of the pulses.

Note that a circuit called an analog front end, which integrates and digitalizes the charges output by the detecting elements 40 and supplies the integration and digitalization result to the collector 14 illustrated in FIG. 1, is provided downstream of the detector 13.

The collector 14 collects count information, which is the result of counting using output signals from the detector 13. Thus, the collector 14 discriminates individual signals output from the detector 13 and collects the count information. The count information is information collected from individual signals output by the detector 13 (the detecting elements 40) each time an X-ray photon having been emitted from the X-ray tube 12a and having passed through the phantom P enters the detector 13. Specifically, the count information is information including a count and an energy level, which are associated with each other, of the X-ray photons incident on the detector 13 (the detecting elements 40). The collector 14 transmits the collected count information to the console 30.

Specifically, the collector 14 collects incidence positions (detected positions) of the X-ray photons counted by discriminating the respective pulses output by the detecting elements 40 and the energy levels of the X-ray photons as the count information at each phase (tube phase) of the X-ray tube 12a. The collector 14 uses positions of the detecting elements 40 that have output pulses (electrical signals) used in counting as the incidence positions, for example. The collector 14 also performs predetermined computation on the electrical signals to measure the energy levels of the X-ray photons.

Next, the bed 20 illustrated in FIG. 1 is an apparatus on which a subject and a phantom P are placed, and includes a top table 22 and a bed driving device 21. The top table 22 is a board on which a subject and a phantom P are placed, and the bed driving device 21 moves the top table 22 in the Z-axis direction to move the subject and the phantom P into the rotatable frame 15.

Note that the gantry 10 performs helical scan of helically scanning the subject or the phantom P by rotating the rotatable frame 15 while moving the top table 22, for example. Alternatively, the gantry 10 performs conventional scan of scanning the subject or the phantom P along a circular path by rotating the rotatable frame 15 with the position of the subject or the phantom P being fixed after moving the top table 22. Alternatively, the gantry 10 performs conventional scan in a step-and-shoot method of performing conventional scan in a plurality of scan areas by moving the position of the top table 22 at regular intervals.

Next, the console 30 has functions of an input unit 31, a display 32, a scan controller 33, a preprocessor 34, a first storage 35, a reconstructor 36, a second storage 37, and a controller 38. The console 30 receives operation of the photon counting CT system made by an operator, and uses the count information collected by the gantry 10 to reconstruct an X-ray CT image.

The input unit 31 transfers information on various instructions and various settings input by the operator of the photon counting CT system through operation of a mouse, a keyboard or the like to the controller 38. For example, the input unit 31 receives a condition on imaging of X-ray CT image data, a reconstruction condition in reconstruction of X-ray CT image data, a condition on image processing of X-ray CT image data, and the like from the operator.

The display 32 is a monitor viewed by the operator, and displays X-ray CT image data and a graphical user interface (GUI) for receiving various instructions, settings, and the like from the operator via the input unit 31 under the control of the controller 38.

The scan controller 33 controls the operations of the irradiation controller 11, the driver 16, the collector 14, and the bed driving device 21 under the control of the controller 38 to control the process of collecting the count information in the gantry 10.

The preprocessor 34 performs correction processes such as a logarithmic transformation process, offset correction, sensitivity correction, and beam hardening correction on the count information sent from the collector 14 to generate projection data.

The first storage 35 stores the projection data generated by the preprocessor 34. Specifically, the first storage 35 stores the projection data (corrected count information) for reconstructing X-ray CT image data.

The reconstructor 36 uses the projection data stored in the first storage 35 to reconstruct X-ray CT image data. There are various methods for reconstruction, including back projection, for example. Examples of the back projection include back projection according to the filtered back projection (FBP) technique. The reconstructor 36 also performs various image processing on the X-ray CT image data to generate image data. The reconstructor 36 stores the reconstructed X-ray CT image data and the image data generated through the image processing into the second storage 37.

Note that the projection data generated from the count information acquired by the photon counting CT system contain information on the energy of X-rays reduced as a result of passing through the phantom P. The reconstructor 36 is thus capable of reconstructing X-ray CT image data of a specific energy component, for example. The reconstructor 36 is also capable of reconstructing X-ray CT image data of each of a plurality of energy components, for example.

The reconstructor 36 is also capable of generating a plurality of X-ray CT image data that are color-coded according to energy components by assigning a tone corresponding to the energy component to each pixel of X-ray CT image data of respective energy components, and further generating image data on which the X-ray CT image data are superimposed.

The controller 38 controls the operations of the gantry 10, the bed 20, and the console 30 to control the whole photon counting CT system. Specifically, the controller 38 controls the scan controller 33 to control CT scan performed by the gantry 10. The controller 38 also controls the preprocessor 34 and the reconstructor 36 to control an image reconstruction process and an image generation process performed by the console 30. The controller 38 also controls display of various image data stored in the second storage 37 onto the display 32.

Figure 3:
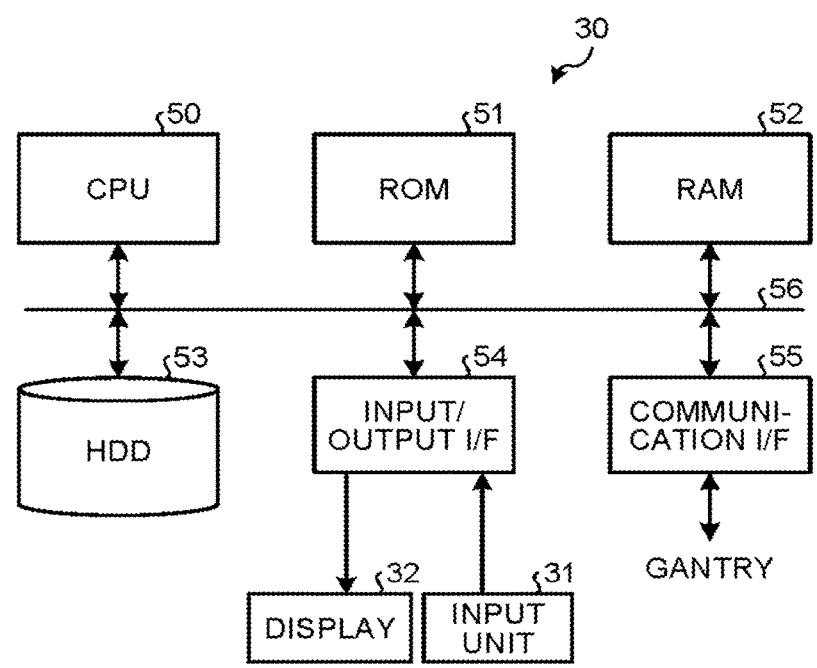
FIG. 3 is a hardware configuration diagram of the photon counting CT system of the first embodiment.

Next, FIG. 3 illustrates a hardware configuration diagram of the console 30. As illustrated in FIG. 3, the console 30 has a hardware configuration similar to that of a common personal computer. Specifically, the console 30 includes a CPU 50, a ROM 51, a RAM 52, an HDD 53, an input/output I/F 54, and a communication I/F 55. The input unit 31 and the display 32 described above are connected to the input/output I/F 54. CPU stands for "Central Processing Unit". ROM stands for "Read Only Memory". RAM stands for "Random Access Memory". HDD stands for "Hard Disk Drive". I/F stands for "Interface".

The CPU 50 to the communication I/F 55 are connected with one another via a bus line 56. The CPU 50 to the communication I/F 55 are connected with one another via a bus line 56. The communication I/F 55 is connected to the gantry 10. The CPU 50 acquires X-ray image data and the like collected by the collector 14 via the communication I/F 55. The scan controller 33, the preprocessor 34, the reconstructor 36, or the controller 38 may be implemented by software in such a manner that the CPU 50 functions according to a program, or may be partly or entirely implemented by hardware. The ROM 51, the RAM 52, and the HDD 53 correspond to the first storage 35 or the second storage 37.

Next, the photon counting CT system of the first embodiment defines a mode of sampled levels of signals output from the detector 13 as a radiation energy zero point (0 keV), and identifies a signal level of characteristic X-ray energy on the basis of a result of measurement of a tube output from the X-ray tube 12a. The photon counting CT system of the first embodiment then calibrates the relation between an output signal from the detector 13 and incident radiation energy by using the two types of information. Such a calibration operation is executed by the CPU 50 operating according to an input/output calibration program stored in the HDD 53, the ROM 51, or the RAM 52 illustrated in FIG. 3.

Note that the input/output calibration program may be recorded on a computer-readable recording medium, which may be provided as a computer program product, such as a CD-ROM or a flexible disk (FD) in a form of a file that can be installed or executed and provided therefrom. Alternatively, the input/output calibration program may be recorded on a computer-readable recording medium such as a CD-R, a DVD, or a semiconductor memory and provided therefrom. DVD stands for "Digital Versatile Disk". Still alternatively, the input/output calibration program may be provided via a network such as the Internet, and the photon counting CT system may download and store the input/output calibration program via the network into a storage such as the ROM 51, the RAM 52 or the HDD 53 for execution. Still alternatively, the input/output calibration program may be embedded in a ROM or the like in the photon counting CT system in advance and provided therefrom.

Figure 4:
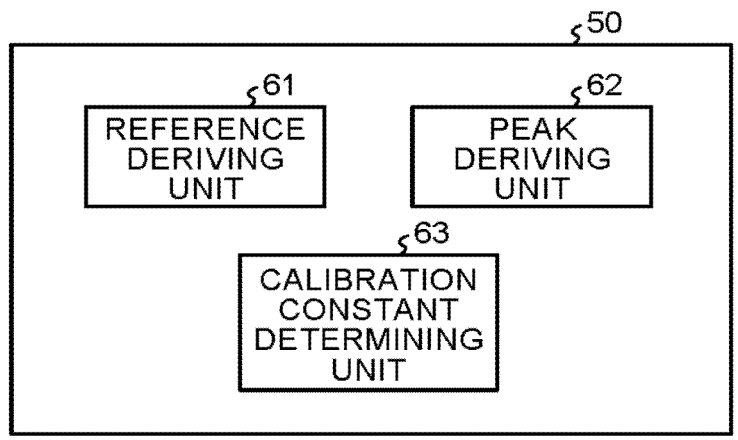
FIG. 4 is a functional block diagram of the photon counting CT system of the first embodiment.

Next, the operator operates the input unit 31 to give an instruction to execute calibration at a desired timing such as before shipment of the photon counting CT system or at the time of maintenance after delivery to a hospital or the like. The CPU 50 is an example of a calibrator. When an instruction to execute calibration is given, the CPU 50 multiplies an electrical signal level output from each of the pixels by a coefficient and adds a first value to the value obtained by the multiplication to calibrate the relation between a detection output from the detector 13 and the radiation incident on the detector 13. Specifically, the CPU 50 reads out the input/output calibration program stored in the HDD 53 or the like, expands functions corresponding to the read input/output calibration program in the RAM 52 or the like, and performs calibration between the input and the output of the detector 13. FIG. 4 is a functional block diagram illustrating the functions provided by the CPU 50 operating according to the input/output calibration program. As illustrated in FIG. 4, the CPU 50 operates according to the input/output calibration program. The CPU 50 includes a reference deriving unit 61, a peak deriving unit 62, and a calibration constant determining unit 63.

Note that the reference deriving unit 61 is an example of a reference calculator that calculates, as the first value, the most frequent electrical signal level from a first set including electrical signal levels output from the respective pixels. The peak deriving unit 62 is an example of a peak calculator that calculates, as a second value, an electrical signal level corresponding to a peak level of the radiation energy of a first characteristic X-ray from the relation between the radiation energy and the radiation intensity obtained from the first set. As will be described below, the peak calculator calculates, as the second value, an average of radiation energy levels within a range including a peak level of the radiation energy of characteristic X-rays. The peak calculator further calculates, as a third value, an electrical signal level corresponding to a peak level of the radiation energy of a second characteristic X-ray from the relation between the radiation energy and the radiation intensity obtained from a second set including other electrical signal levels output from the respective pixels, and a coefficient calculator calculates, as a coefficient, a value representing an amount of change in the radiation energy to an electrical signal level by using the first value, the second value, and the third value. The calibration constant determining unit 63 is an example of the coefficient calculator that calculates the coefficient by dividing the difference between the first value and the second value by the peak level of the radiation energy of the characteristic X-ray. In this example, description is continued on the assumption that the reference deriving unit 61, the peak deriving unit 62, and the calibration constant determining unit 63 are implemented by software according to the input/output calibration program; alternatively, the units may be partly or entirely implemented by hardware.

Figure 5:
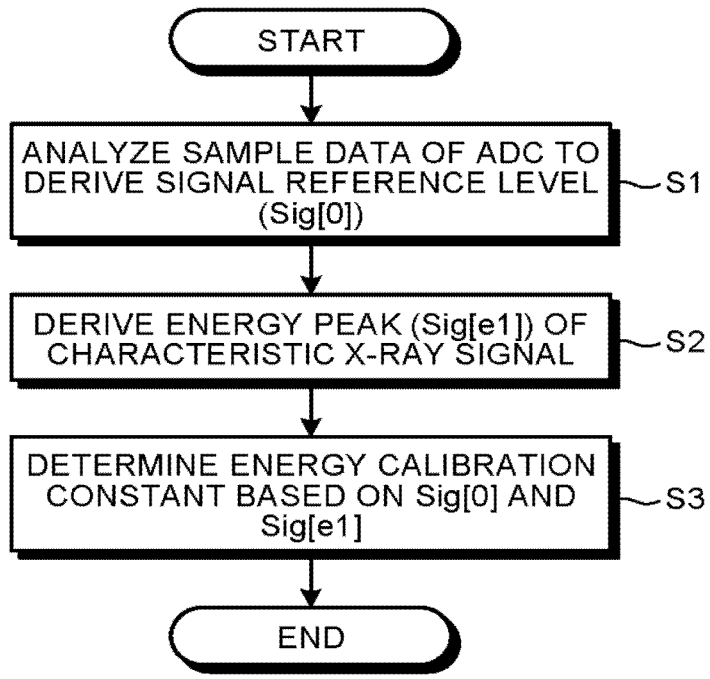
FIG. 5 is a flowchart illustrating a flow of an input/output calibration process of a detector provided in the photon counting CT system of the first embodiment.

FIG. 5 is a flowchart illustrating a calibration process flow. First, before performing the calibration process, the operator emits X-rays to a target having a known characteristic X-ray energy level such as a tungsten target or a molybdenum target to acquire an X-ray energy spectrum (X-ray sampling data from an analog-to-digital converter (ADC)). X-ray sampling data corresponding to the X-ray energy spectrum are generated by an analog-to-digital converting circuit (ADC) provided in what is called an analog front end of the detector 13, and stored in a storage such as the HDD 53 illustrated in FIG. 3 via the collector 14 illustrated in FIG. 1.

The calibration process illustrated in the flowchart of FIG. 5 is performed using the X-ray energy spectrum store in the HDD 53 in this manner. Thus, a step of acquiring the X-ray energy spectrum and a step of performing the calibration process need not necessarily be successive. Specifically, the calibration process may be performed at an interval such as several hours or several days after acquisition of the X-ray energy spectrum. In addition, the acquired X-ray energy spectrum may be stored in a storage medium such as a CD-ROM, a DVD, or a semiconductor memory, and the X-ray energy spectrum may be read from the storage medium for the calibration process.

Figure 6A:
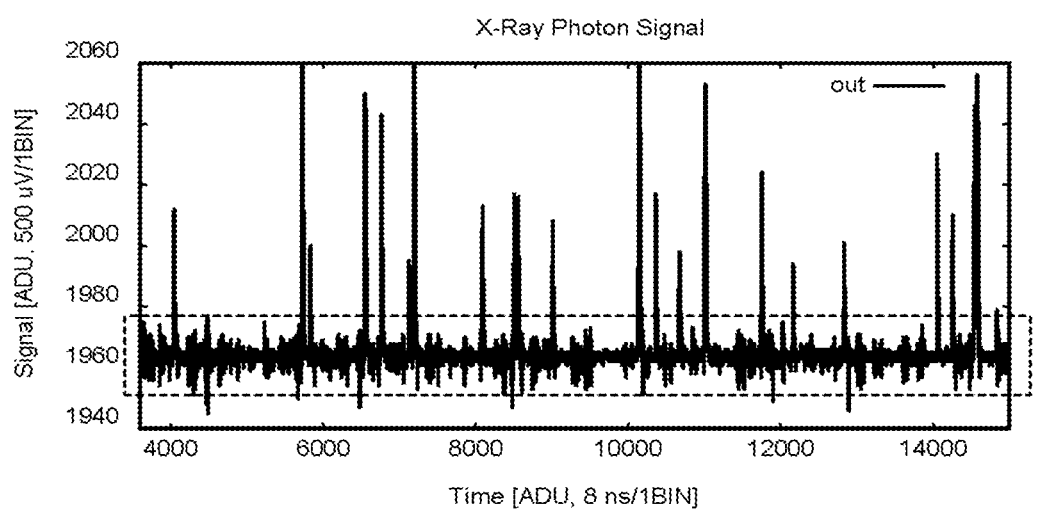
FIG. 6A is a graph illustrating an example of an X-ray energy spectrum in the photon counting CT system of the first embodiment.
Figure 6B:
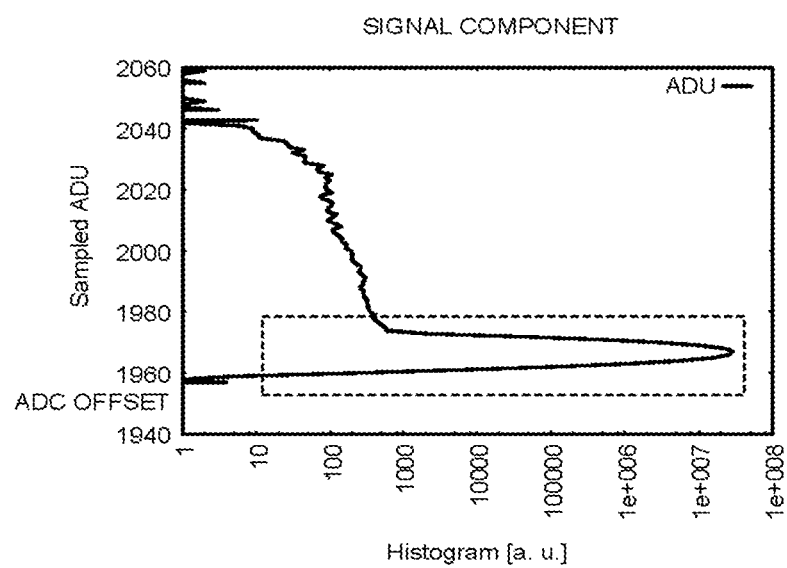
FIG. 6B is a graph illustrating occurrence rates of respective acquired X-ray levels in the photon counting CT system of the first embodiment.

Subsequently, after the X-ray energy spectrum is acquired and an instruction to start the calibration process is given by the operator, the reference deriving unit 61 illustrated in FIG. 4 analyzes the acquired X-ray energy spectrum to derive a signal reference level (Sig[0]) in step S1 of the flowchart of FIG. 5. Specific details are as follows. FIG. 6A is a graph illustrating an example of the X-ray energy spectrum. FIG. 6B is a graph illustrating occurrence rates of the respective acquired X-ray levels.

In step S1, the reference deriving unit 61 calculates an average of a range including the most frequently occurring value (mode) in the X-ray sampling data, and defines the calculated value as an offset (an X-ray energy zero point (0 keV)), for example. Specifically, the average of the sampling data in a range including the most frequently occurring value (mode) in the X-ray sampling data, such as a range from a value smaller than the mode by three to a value larger than the mode by three, is calculated, and the calculated value is defined as an offset (an X-ray energy zero point (0 keV)). Boxes in dot lines in FIGS. 6A and 6B represent sampling data around the mode to be used for the calculation of the aforementioned average among the X-ray sampling data. While the average around the mode is derived as a signal reference level (Sig[0]) in this example, the mode itself may alternatively be derived as a signal reference level (Sig[0]).

Figure 7A:
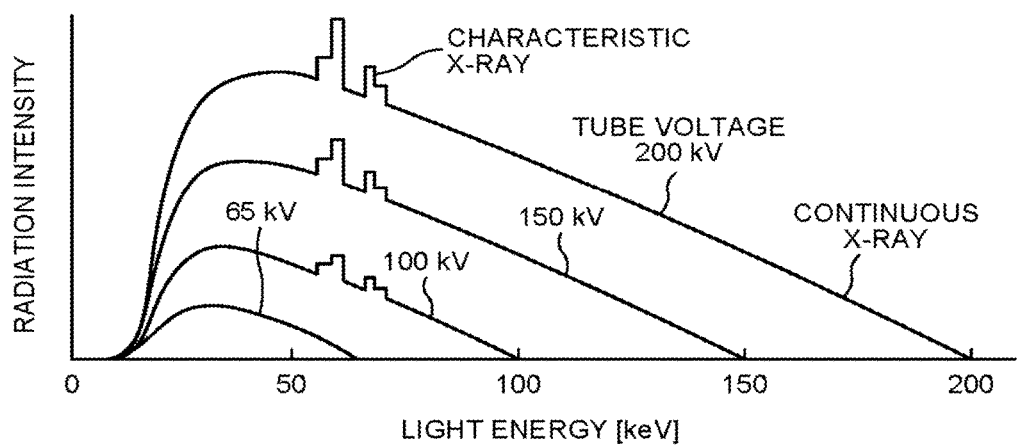
FIG. 7A is a graph illustrating an energy level at which a characteristic X-ray signal in a tungsten target X-ray tube occurs in the photon counting CT system of the first embodiment.
Figure 7B:
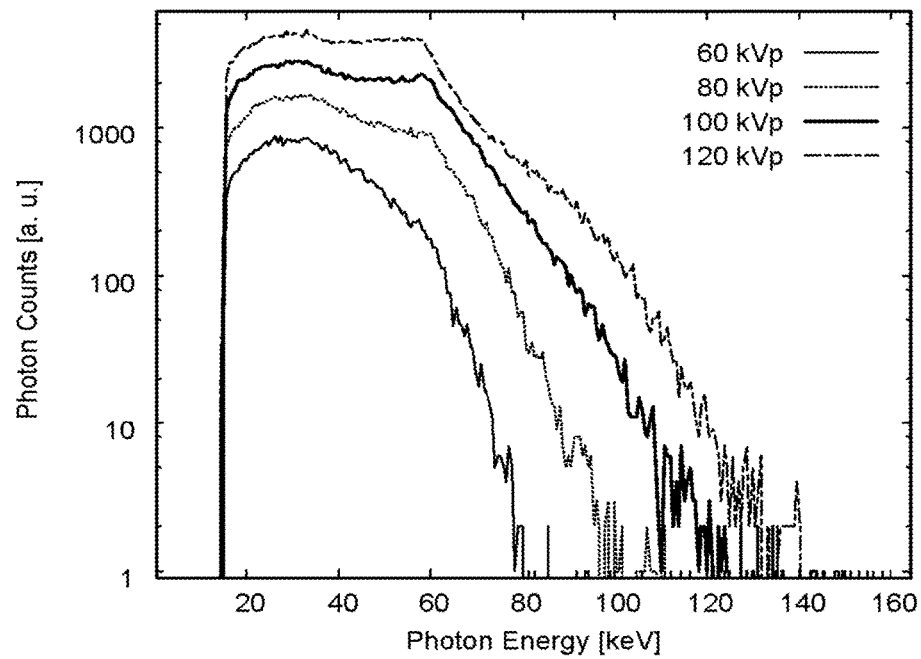
FIG. 7B is another graph illustrating an energy level at which a characteristic X-ray signal in a tungsten target X-ray tube occurs in the photon counting CT system of the first embodiment.

Subsequently, in step S2, the peak deriving unit 62 derives a peak position of a characteristic X-ray signal as an energy peal (Sig[e1]). FIG. 7A is a graph illustrating an energy level at which a characteristic X-ray signal occurs in a tungsten target X-ray tube. FIG. 7B is another graph illustrating an energy level at which a characteristic X-ray signal occurs in a tungsten target X-ray tube. In the case of the tungsten target X-ray tube, as illustrated in FIGS. 7A and 7B, a characteristic X-ray signal occurs at an energy level of about 60 keV. Thus, the peak deriving unit 62 calculates the average of some sampling data larger and smaller than the energy level of about 60 keV included in a range around the energy level of about 60 keV, and defines the calculated value as the energy peak (Sig[e1]) of the characteristic X-ray signal.

Figure 8:
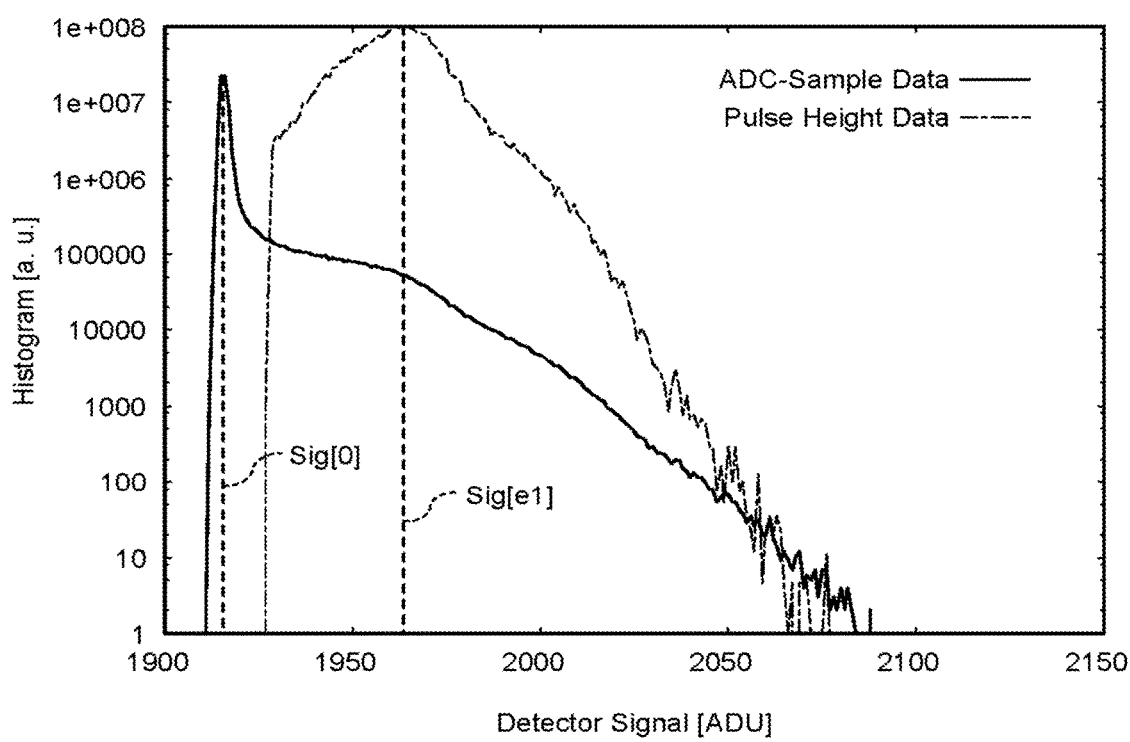
FIG. 8 is a graph illustrating an example of a signal reference level and a peak level calculated by the photon counting CT system of the first embodiment.

As a result, as illustrated in FIG. 8, the signal reference level (Sig[0]) of the detector 13 and the energy peak (Sig[e1]) of the characteristic X-ray signal are determined.

Subsequently, in step S3, the calibration constant determining unit 63 uses the signal reference level (Sig[0]) of the detector 13 and the energy peak (Sig[e1]) of the characteristic X-ray signal to determine an energy calibration constant for calibration of the relation between the incident X-ray energy and the output of the detector 13, and terminates the process of the flowchart of FIG. 5. Specifically, the relation between the incident X-ray energy and the output of the detector 13 is calibrated by an arithmetic expression of "Signal (ADU)=a(Photon_Energy (keV))+b". Note that "ADU" refers to a value of sampling data of incident X-rays in the analog-to-digital converting circuit; "keV" is a unit of X-ray energy.

The calibration constant determining unit 63 calculates a coefficient of "a" and a coefficient of "b" in the calibration expression. Specifically, the calibration constant determining unit 63 performs computation of "coefficient a=(Sig[e1]−Sig[0])/e1 (ADU/keV)" to calculates the "coefficient a" representing a weight of X-ray energy of 1 (keV). "e1" represents a value of the energy peak of the characteristic X-ray signal. The calibration constant determining unit 63 also performs computation of "coefficient b=Sig[0] (ADU)" to calculate the "coefficient b" representing a signal reference level (a base line) of the detection outputs of the detector 13.

After calculating the calibration constants (the coefficient a and the coefficient b) in this manner, the CPU 50 uses the arithmetic expression "Signal (ADU)=a(Photon_Energy (keV))+b" to calibrate the relation between the incident X-ray energy and the output of the detector 13. As a result, the detection outputs of the detector 13 (the sampling data of the ADC) can be converted to values corresponding to the differences between the energy peak level of the characteristic X-ray signal and the signal reference levels of the sampling data by the "coefficient a". In addition, the coefficient b is added to the values obtained by the conversion by the "coefficient a", so that the detection outputs of the detector 13 (the sampling data of the ADC) can be changed to values adjusted with reference to the signal reference levels.

Figure 9A:
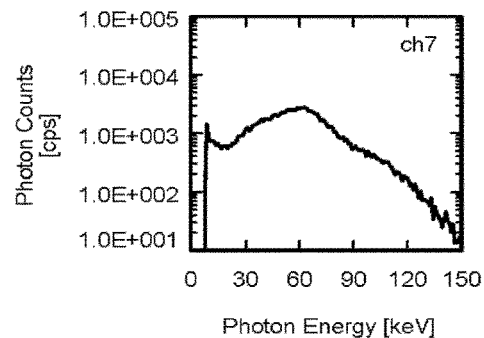
FIG. 9A is a graph illustrating a change in the number of radiation photons in a detector where calibration is not performed, and illustrating a change in the number of radiation photons of a detecting element of channel #7.
Figure 9B:
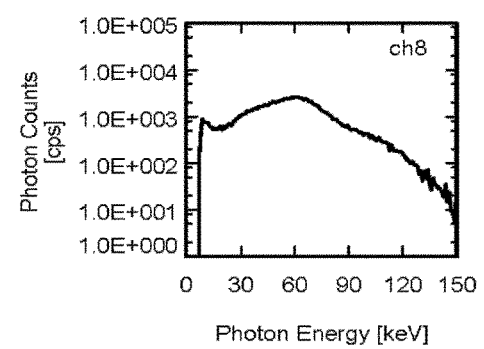
FIG. 9B is a graph illustrating a change in the number of radiation photons in the detector where calibration is not performed, and illustrating a change in the number of radiation photons of a detecting element of channel #8.
Figure 9C:
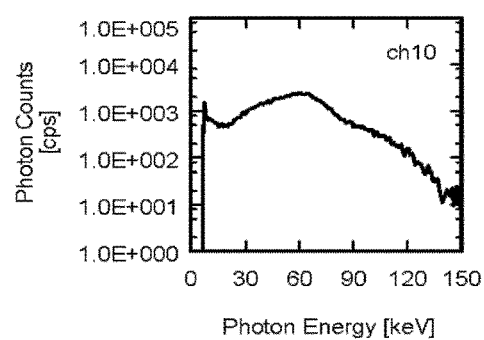
FIG. 9C is a graph illustrating a change in the number of radiation photons in the detector where calibration is not performed, and illustrating a change in the number of radiation photons of a detecting element of channel #10.
Figure 9D:
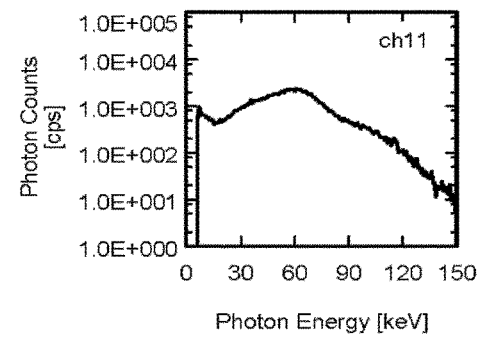
FIG. 9D is a graph illustrating a change in the number of radiation photons in the detector where calibration is not performed, and illustrating a change in the number of radiation photons of a detecting element of channel #11.
Figure 9E:
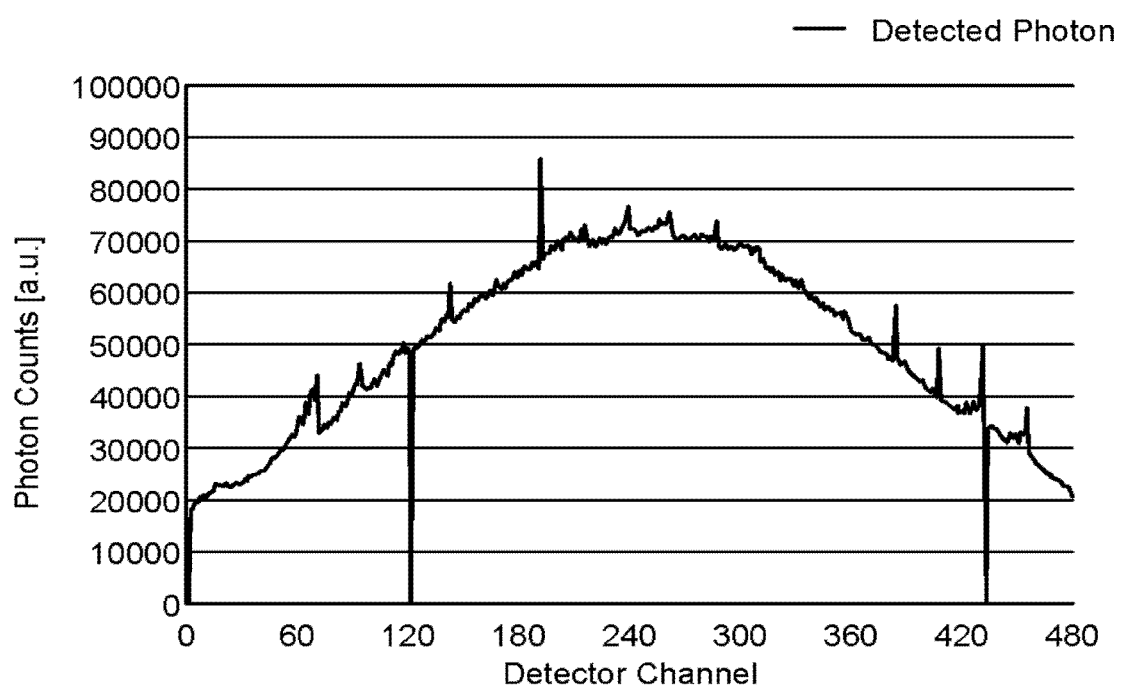
FIG. 9E is a graph illustrating a change in the number of radiation photons in the detector where calibration is not performed, and illustrating, for each channel, a sum of the numbers of radiation photons in the whole energy range of the channel.

FIGS. 9A to 9E are graphs illustrating changes in the number of radiation photons in a detector where calibration is not performed. FIG. 9A illustrates a change in the number of radiation photons of a detecting element of channel #7 (ch7), where the horizontal axis represents the photon energy level (Photon Energy; unit: keV) and the vertical axis represents the radiation intensity (Photon Counts; unit: cps). Similarly, FIG. 9B illustrates a change in the number of radiation photons of a detecting element of channel #8 (ch8). Similarly, FIG. 9C illustrates a change in the number of radiation photons of a detecting element of channel #10 (ch10). Similarly, FIG. 9D illustrates a change in the number of radiation photons of a detecting element of channel #11 (ch11). Furthermore, FIG. 9E is a graph obtained by detecting and plotting, for each channel, a sum of the numbers of radiation photons in the whole energy range (0 keV to 150 keV) of the channel, where the horizontal axis represents the channel (identification) number of the detector and the vertical axis represents the number of radiation photons (Photon Counts; unit: a.u.). Note that the example of FIG. 9E is an example in which the number of channels of a detector is 480.

As can be seen in FIGS. 9A to 9E, in the case of a detector where calibration is not performed, variations are caused in the outputs of channels at lower energy levels as illustrated in FIGS. 9A to 9D owing to variations in the characteristics of the channels and variations in geometric structures in view of the sums of the numbers of radiation photons of the whole energy (0 keV to 150 keV). Thus, the numbers of radiation photons when the photon energy levels are low differ from channel to channel. Such variations in the outputs of the channels appear as spike noise (artifact) as illustrated in FIG. 9E.

Figure 10A:
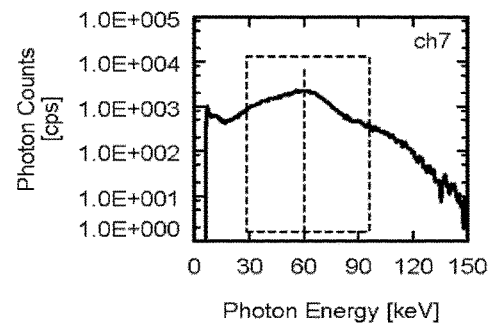
FIG. 10A is a graph illustrating a change in the number of radiation photons in a detector where calibration is performed, and illustrating a change in the number of radiation photons of a detecting element of channel #7.
Figure 10B:
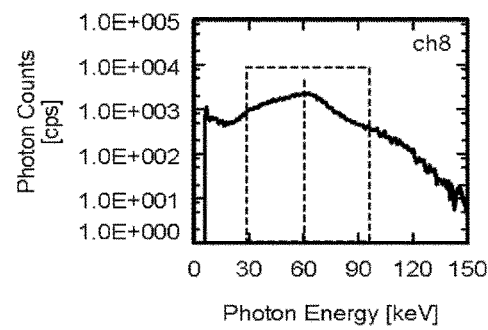
FIG. 10B is a graph illustrating a change in the number of radiation photons in the detector where calibration is performed, and illustrating a change in the number of radiation photons of a detecting element of channel #8.
Figure 10C:
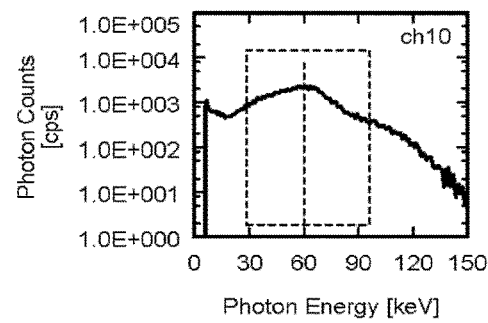
FIG. 10C is a graph illustrating a change in the number of radiation photons in the detector where calibration is performed, and illustrating a change in the number of radiation photons of a detecting element of channel #10.
Figure 10D:
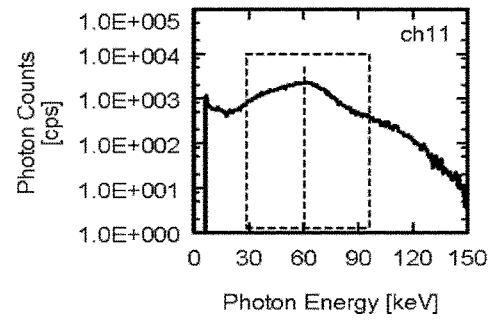
FIG. 10D is a graph illustrating a change in the number of radiation photons in the detector where calibration is performed, and illustrating a change in the number of radiation photons of a detecting element of channel #11.
Figure 10E:
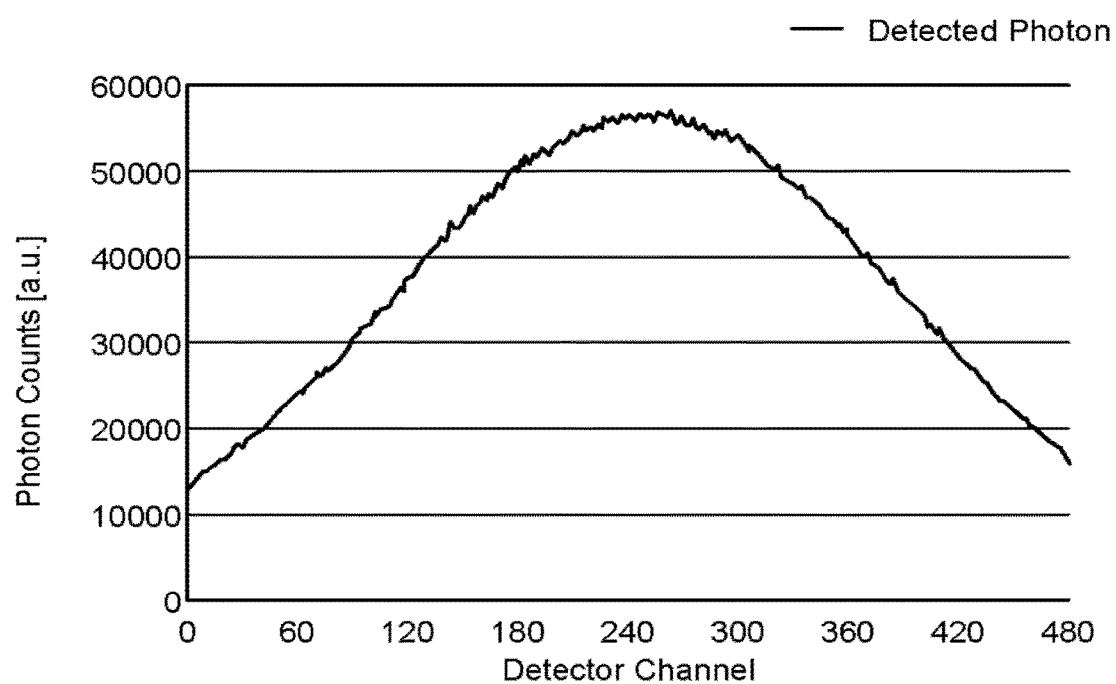
FIG. 10E is a graph illustrating a change in the number of radiation photons in the detector where calibration is performed, and illustrating, for each channel, a sum of the numbers of radiation photons in the whole energy range of the channel.

In contrast, FIGS. 10A to 10E are graphs illustrating changes in the number of radiation photons in the detector 13 of the photon counting CT system of the first embodiment where calibration is performed as described above. FIG. 10A illustrates a change in the number of radiation photons of different detecting elements of channel #7 (ch7), where the horizontal axis represents the photon energy level (Photon Energy; unit: keV) and the vertical axis represents the radiation intensity (Photon Counts; unit: cps). Similarly, FIG. 10B illustrates a change in the number of radiation photons of detecting elements of channel #8 (ch8). Similarly, FIG. 10C illustrates a change in the number of radiation photons of detecting elements of channel #10 (ch10). Similarly, FIG. 10D illustrates a change in the number of radiation photons of detecting elements of channel #11 (ch11). Furthermore, FIG. 10E is a graph obtained by detecting and plotting, for each channel, a sum of the numbers of radiation photons in the whole energy range (0 keV to 150 keV) of the channel, where the horizontal axis represents the channel (identification) number of the detector 13 and the vertical axis represents the number of radiation photons (Photon Counts; unit: a.u.). Note that the example of FIG. 10E is an example in which the number of channels of the detector 13 is 480. Furthermore, FIG. 10E is a graph illustrating outputs of the respective channels obtained by selectively adding the radiation photons of the respective channels in an energy range of 30 keV to 90 keV as indicated by boxes in dotted lines in FIGS. 10A to 10D.

As a result of the calibration of the input/output of the detector 13 as described above, variations in the characteristics of the respective channels such as variations in the characteristics (multiplication rate, operating temperatures, etc.) of the photomultiplier elements and variations in the scintillation light detection efficiency (variations in the detector geometric structure) can be reduced as can be seen in FIGS. 10A to 10E. Thus, as illustrated in FIG. 10E, detection outputs having ideal characteristics where spike noise (artifact) is reduce are achieved as the outputs of the detector 13.

As is clear from the description above, the photon counting CT system of the first embodiment identifies the mode of sampling data of X-ray detection outputs of the detector 13 to calculate a signal reference level (energy zero point: Sig[0]). In addition, a peak (Sig[e1]) of characteristic X-ray energy associated with an X-ray tube target. Furthermore, the sampling data of the respective detecting elements are multiplied by a value, which is the coefficient a, obtained by dividing a difference between the signal reference level (Sig[0]) and the energy peak (Sig[e1]) of the characteristic X-ray signal by the energy peak level (e1) of the characteristic X-ray signal. As a result, the detection outputs of the detector 13 (the sampling data of the ADC) can be converted to values corresponding to the differences between the energy peak level of the characteristic X-ray signal and the signal reference levels of the sampling data by the "coefficient a". In addition, the coefficient b is added to the values obtained by the conversion by the "coefficient a", so that the detection outputs of the detector 13 (the sampling data of the ADC) can be changed to values adjusted with reference to the signal reference levels.

Such calibration determines parameters of the coefficients a and b by the sampling data of X-ray detection outputs of the detector 13 and mode identification of an energy peak level of a characteristic X-ray signal. Thus, the same calibration process as described with reference to the aforementioned expression can be applied to all of the detecting elements of the detector 13. This therefore allows full automation of calibration. In addition, since calibration can be performed with a simple arithmetic expression, this enables simple and high-speed calibration as compared to calibration using a calibration source.

Second Embodiment

Next, a photon counting CT system of a second embodiment will be described. In the second embodiment, a K-absorption edge of predetermined metal is used in place of the energy peak (Sig[e1]) of a characteristic X-ray signal described in the first embodiment. Note that the first embodiment described above and the second embodiment below are different from each other only in this regard. Thus, only the difference therebetween will be described below, and the same description will not be repeated.

Figure 11:
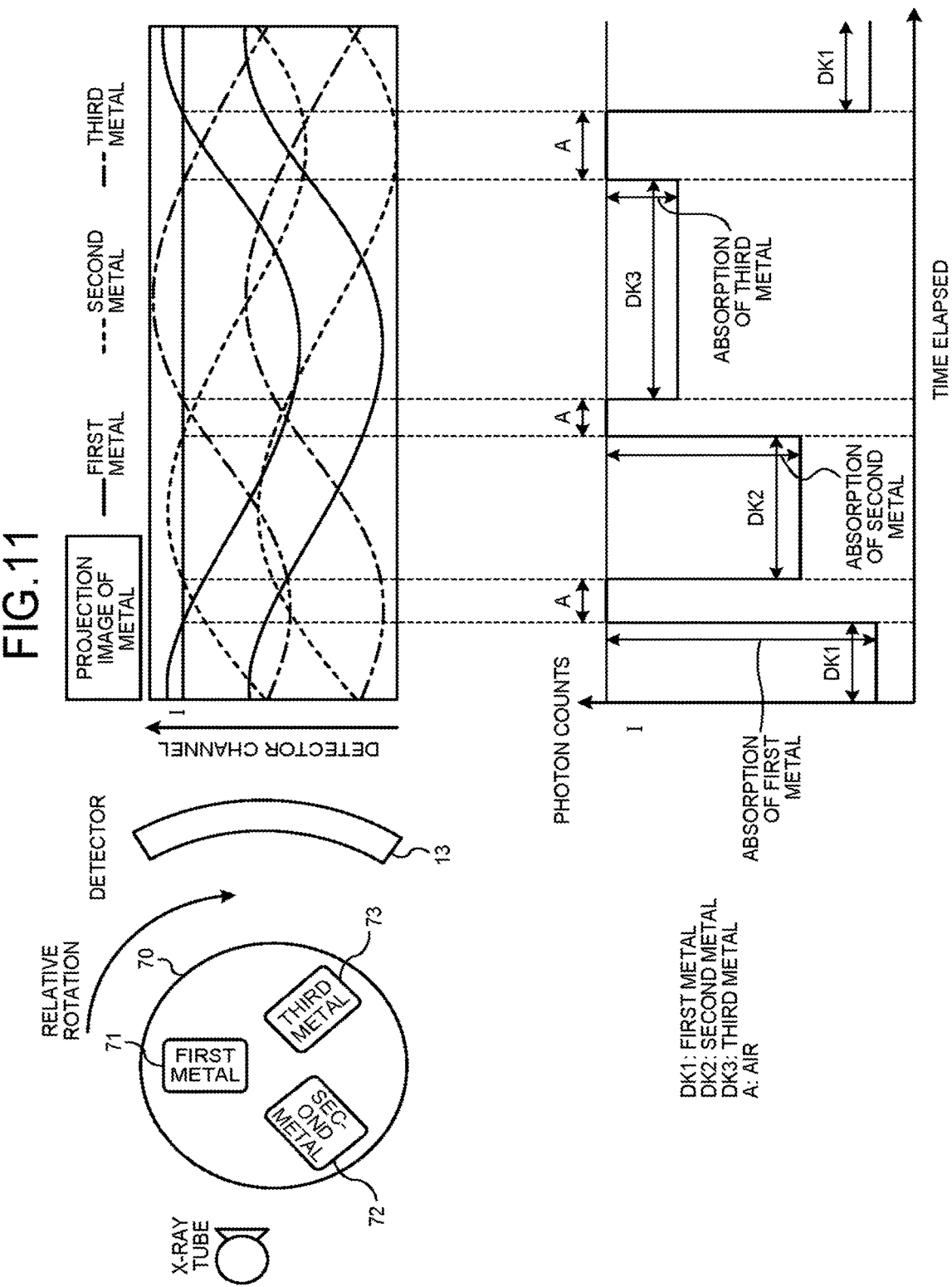
FIG. 11 is a diagram illustrating an example of a phantom imaged by a photon counting CT system of a second embodiment and a projection image.

In the case of the second embodiment, as illustrated in FIG. 11, a phantom 70 provided with one or more metals is used. In the example illustrated in FIG. 11, the phantom 70 is provided with first metal 71 to third metal 73. Examples of the metals include gold, tungsten, and molybdenum. The first to third metals 71 to 73 are arranged in the phantom 70 in such a manner that the metals can be imaged by rotating a substantially cylindrical phantom 70 one or more revolutions. While the phantom 70 is rotated in this example, alternatively, the X-ray tube 12a and the detector 13 may be rotated. In addition, while three metals 71 to 73 are provided in the phantom 70, alternatively, any one, two of the metals or four or more metals may be provided.

As illustrated in FIG. 11, projection images corresponding to the first to third metals 71 to 73 can be acquired by rotation of the phantom 70 in the relation of the phantom 70 and the detector 13 during X-ray emission. Specifically, in FIG. 11, in a graph illustrating a plurality of sine-curve waveforms, the vertical axis represents the channels of the detector 13 and the horizontal axis represents time elapsed from start of measurement. The sine-curve waveforms represent projection images corresponding to the first to third metals 71 to 73 detected by a detecting element of a channel (channel I) provided at a position I of the detector 13. A sine-curve waveform in a solid line represents a projection image of the first metal 71. A sine-curve waveform in a dotted line represents a projection image of the second metal 72. A sine-curve waveform in a long dashed short dashed line represents a projection image of the third metal 73.

The number of X-ray photons passing through a subject, that is, the photon count of the detector 13 changes depending on the magnitude of the attenuation coefficient of the subject. Thus, the magnitudes of the numbers of detected photons corresponding to the metals provided in the phantom 70 appear as a trajectory as a result of the rotation of the phantom 70. Specifically, when the photon count of a channel I of the detector 13 in the elapsed time direction is measured, such a graph as that of square waves in FIG. 11 is obtained. As can be seen from the graph of square waves, the magnitudes of the photon counts are different depending on the metals to which X-rays are emitted. "DK1" in the graph of the square waves represents an interval during which X-rays are emitted to the first metal 71. In this example, since the X-ray attenuation coefficient of the first metal 71 is large, the photon count of the detector 13 is small. "DK2" in the graph of the square waves represents an interval during which X-rays are emitted to the second metal 72. In this example, since the X-ray attenuation coefficient of the second metal 72 is medium, the photon count of the detector 13 is also medium. "DK3" in the graph of the square waves represents an interval during which X-rays are emitted to the third metal 73. In this example, since the X-ray attenuation coefficient of the third metal 73 is small, the photon count of the detector 13 is large.

Furthermore, "A" in the graph of the square waves represents an interval during which X-rays are emitted to the detector 13 via a gap (air) between the metals 71 to 73. In this case, since X-rays are emitted to the detector 13 without being attenuated by a metal or the like, the photon count is larger than those in the emission intervals DK1 to DK3.

The photon counts with the metals 71 to 73 obtained in this manner are put together to form a pulse height distribution, which allows X-ray absorptions associated with the respective metals 71 to 73 to be captured. The CPU 50 divides the transmission spectra by the pulse height spectrum obtained in the emission interval "A" described above to obtain absorption spectra for the first to third metals 71 to 73. The pulse height spectrum of the air may be obtained by a separate measurement. The CPU 50 captures the peaks of the absorption spectra as K-absorption edges of the metal, and plots the relations of the energy and the pulse height. As a result, similarly to the first embodiment described above, calibration of the input/output energy of the detector 13 can be performed.

While FIG. 11 is a graph illustrating the photon counts of a channel I of the detector 13, a channel where it is difficult to detect a photon count for a gap (air) between the metals 71 to 73 is present among the channels of the detector 13. FIG. 12 illustrates that a channel II of the detector 13 is a channel where it is difficult to detect a photon count for a gap (air) between the metals 71 to 73. Specifically, as illustrated in a graph of a plurality of sine-curve waveforms in FIG. 12, in the case of the channel II of the detector 13, the projection images of the metals 71 to 73 overlap one another in a complicated manner, a gap (air) between the metals 71 to 73 is less likely to be formed, and it is difficult to detect the photon count for the gap (air).

More specifically, in the case of the channel II of the detector 13, the projection images of the metals 71 to 73 are detected in a state in which the projection images overlap one another in a complicated manner, such as an emission interval DK1 corresponding to the second metal+the third metal→an emission interval DK2 corresponding to the third metal→an emission interval DK3 corresponding to the first metal+the third metal→an emission interval DK4 corresponding to the first metal→an emission interval DK5 corresponding to the first metal+the second metal→an emission interval DK6 corresponding to the second metal→an emission interval DK7 corresponding to the second metal+the third metal . . . and so on as illustrated in the graph of square waves in FIG. 12. A projection image of each metal alone can be detected in the emission intervals DK2, DK4, DK6, . . . , but projection images of a plurality of metals overlapping one another (the first metal+the second metal, for example) are detected in the other emission intervals DK1, DK3, DK5, DK7, . . . , and it is difficult to detect a projection image corresponding to a gap (air) between the metals 71 to 73.

In such a case, the CPU 50 performs the above-described computation by using a pulse height spectrum of the air obtained separately to calculate the absorption spectra. The absorption spectra of the metals can be obtained from a pulse height spectrum of each metal alone and a pulse height spectrum of the air. As a result, the above-described computation is enabled even for a channel where it is difficult to detect a projection image corresponding to a gap (air) between the metals 71 to 73.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation measuring apparatus comprising:
   a detector having a plurality of pixels each including a plurality of detecting elements each configured to output an electrical signal level associated with incident radiation energy;
   a reference calculator configured to calculate, as a first value, a most frequent electrical signal level from a first set of electrical signal levels output from the first respective pixels;
   a peak calculator configured to calculate, as a second value, an electrical signal level corresponding to a peak level of radiation energy of a first characteristic X-ray, based on a relation between a radiation energy and a radiation intensity obtained from the first set;
   a coefficient calculator configured to calculate a coefficient obtained by dividing a difference between the first value and the second value by the peak level of the radiation energy of the first characteristic X-ray; and
   a calibrator configured to multiply an electrical signal level output from each of the pixels by the coefficient and add the first value to a value obtained by the multiplication to calibrate a relation between a detection output of the detector and radiation incident on the detector.

2. The apparatus according to claim 1, wherein the peak calculator calculates, as the second value, an average of radiation energy levels in a range including the peak level of the radiation energy of the first characteristic X-ray.

3. The apparatus according to claim 2, wherein
   the peak calculator further calculates, as a third value, an electrical signal level corresponding to a peak level of radiation energy of a second characteristic X-ray, based on a relation between radiation energy and radiation intensity obtained from a second set of other electrical signal levels output from the second respective pixels, and
   the coefficient calculator calculates, as the coefficient, a value representing an amount of change in the radiation energy relative to the electrical signal levels by using the first value, the second value, and the third value.

4. A computer program product comprising a non-transitory computer-readable medium containing a program, wherein the program, when executed by a computer, causes the computer to execute:
   calculating, as a first value, a most frequent electrical signal level from a first set of electrical signal levels output from a plurality of pixels of a detector, each pixel including a plurality of detecting elements each configured to output an electrical signal level associated with incident radiation energy;

calculating, as a second value, an electrical signal level corresponding to a peak level of radiation energy of a first characteristic X-ray, based on a relation between a radiation energy and a radiation intensity obtained from the first set;

calculating a coefficient obtained by dividing a difference between the first value and the second value by the peak level of the radiation energy of the first characteristic X-ray; and multiplying an electrical signal level output from each of the pixels by the coefficient and adding the first value to a value obtained by the multiplication to calibrate a relation between a detection output of the detector and radiation incident on the detector.

5. The computer program product according to claim 4, wherein an average of radiation energy levels in a range including the peak level of the radiation energy of the first characteristic X-ray is calculated as the second value.

6. The computer program product according to claim 5, further comprising calculating, as a third value, an electrical signal level corresponding to a peak level of radiation energy of a second characteristic X-ray, based on a relation between radiation energy and radiation intensity obtained from a second set of other electrical signal levels output from second respective pixels, wherein a value representing an amount of change in the radiation energy relative to the electrical signal levels by using the first value, the second value, and the third value is calculated as the coefficient.

7. A radiation computed tomography apparatus comprising:

an irradiator configured to emit radiation;

a detector having a plurality of pixels each including a plurality of detecting elements each configured to output an electrical signal level associated with incident radiation energy;

a reference calculator configured to calculate, as a first value, a most frequent electrical signal level from a first set of electrical signal levels output from first respective pixels;

a peak calculator configured to calculate, as a second value, an electrical signal level corresponding to a peak level of radiation energy of a first characteristic X-ray, based on a relation between a radiation energy and a radiation intensity obtained from the first set;

a coefficient calculator configured to calculate a coefficient obtained by dividing a difference between the first value and the second value by the peak level of the radiation energy of the first characteristic X-ray;

a calibrator configured to multiply an electrical signal level output from each of the pixels by the coefficient and add the first value to a value obtained by the multiplication to calibrate a relation between a detection output of the detector and radiation incident on the detector; and a reconstructor configured to reconstruct a radiation computed tomography image by using the detection output of the detector.

* * * * *